US006235958B1

(12) United States Patent
Commereuc et al.

(10) Patent No.: US 6,235,958 B1
(45) Date of Patent: May 22, 2001

(54) PROCESS FOR CONVERTING $C_5$ OLEFINIC CUTS BY METATHESIS USING A CATALYST BASED ON RHENIUM AND CESIUM

(75) Inventors: Dominique Commereuc, Meudon; François Hugues, Vernaizon; Lucien Saussine, Croissy sur Seine, all of (FR)

(73) Assignee: Institut Francais du Petrole (FR)

( * ) Notice: Subject to any disclaimer, the term of this patent is extended or adjusted under 35 U.S.C. 154(b) by 0 days.

(21) Appl. No.: 09/412,568

(22) Filed: Oct. 5, 1999

(30) Foreign Application Priority Data

Oct. 5, 1998 (FR) .................................................. 98 12470

(51) Int. Cl.$^7$ ........................................................ C07C 6/00
(52) U.S. Cl. .......................... 585/647; 585/644; 585/646
(58) Field of Search ................................. 585/644, 646, 585/647; 502/344, 201, 218, 224

(56) References Cited

U.S. PATENT DOCUMENTS 3,658,927 * 4/1972 Crain et al. ........................... 585/647
5,304,692 * 4/1994 Yamada et al. ...................... 585/646

FOREIGN PATENT DOCUMENTS 0 691 318 A1   1/1996  (EP) .
0 742 195 A1   11/1996 (EP) .

* cited by examiner

Primary Examiner—Marian C. Knode
Assistant Examiner—Thuan D. Dang
(74) Attorney, Agent, or Firm—Millen, White, Zelano & Branigan, P.C.

(57) ABSTRACT

The present invention provides a process for converting olefinic $C_5$ cuts by metathesis using an improved catalyst containing rhenium, cesium, and delta alumina. The preferred catalysts contains at least one rhenium compound deposited on a support principally composed of alumina, treated at a temperature of more than 750° C., and modified by at least one cesium compound. Thus the duration of the cycle between two regeneration operations is substantially increased.

20 Claims, No Drawings

PROCESS FOR CONVERTING C$_5$ OLEFINIC CUTS BY METATHESIS USING A CATALYST BASED ON RHENIUM AND CESIUM

The invention relates to a process for metathesis of olefinic C$_5$ cuts (i.e., containing pentenes) with a catalyst comprising delta alumina, rhenium and cesium.

Preferably, the present invention provides a process for converting a C$_5$ hydrocarbon cut as defined above, after selective hydrogenation of diolefins and acetylenic compounds and hydroisomerisation of monoolefins, by metathesis with ethylene or propylene in the presence of a catalyst based on rhenium improved by the incorporation of cesium and by the presence of delta alumina.

Cracking light paraffins produces ethylene and propylene required for petrochemistry. It also produces a certain number of other products including a C$_5$ hydrocarbon cut which principally contains C$_5$ diolefins, methylbutenes, n-pentenes and pentane, also traces of acetylenic hydrocarbons.

The metathesis reaction converts such cuts, which are often inadequately used, to compounds with a higher intrinsic value. As an example, metathesis with ethylene or propylene of an olefinic C$_5$ cut, which has already undergone selective hydrogenation of diolefins and acetylenic compounds and hydroisomerisation of monoolefins, can produce isobutene, a compound which is in great demand for synthesising methyl tertio-butyl ether for use as a fuel additive or for polymerisation.

When such a reaction is carried out using the usual rhenium-based metathesis catalysts, olefins such as the isobutene produced and the 2-methyl-2-butene contained in the C$_5$ cut polymerise on contact with the catalyst and that secondary reaction causes a large reduction in duration of the cycle for the catalyst between two regeneration operations.

Incorporating alkali metals into a rhenium-based metathesis catalyst to carry out metathesis of C$_5$ olefins has been described in European patent EP-A-0 691 318, although no mention is made of the importance of using any particular alkali metal over any others.

Incorporating cesium into a rhenium-based metathesis catalyst has been described in French patent FR-A-2 373 504, for the preparation of branched olefins. In U.S. Pat No. 5,057,644, cesium has been cited as a possible additional alkaline element in a catalyst activated at 300–600° C. brought into the presence of organic borane as a promoter. FR-A-1 572 314 indicates that the selectivity of a metathesis catalyst can be increased by adding cesium in particular, and that activation occurs at 300–750° C.

The alumina used as a support in the prior art is generally a gamma alumina and the catalyst is heat activated in a temperature range which usually does not exceed 750° C., although U.S. Pat. No. 3,594,440 indicates that it is possible to go up to 900° C., with no mention of a particular advantage. In a more recent publication, it is indicated that there is no interest in activating a cesium-rhenium-alumina catalyst at a temperature of more than 300° C., the catalyst being prepared by impregnating rhenium into alumina, calcining at 550° C., introducing cesium by impregnation, calcining at 500° C., then activating in nitrogen (T. Kawai et al., Journal of Molecular Catalysis, vol. 76, pp. 249–261, 1992).

SUMMARY OF THE INVENTION

We have now discovered that the use of a rhenium- and cesium-based metathesis catalyst which has previously been activated at a temperature of more than 750° C. leads to a substantial reduction in the deactivation rate, without substantially affecting the activity for the metathesis reaction, which substantially increases the duration of cycles between two regeneration steps.

Without wishing to be bound by a particular interpretation, heat activation of a gamma alumina at temperatures beyond 750° C., and generally of at most 1000° C., is known to partially transform it into delta alumina. The beneficial effect on performance could be considered to be attributed to the presence of this type of alumina combined with the presence of cesium.

More precisely, the process forming the subject matter of the invention concerns a process for converting an olefinic C$_5$ cut by metathesis, either with ethylene to produce an effluent containing principally propylene, isobutene and n-butenes, or with propylene to produce an effluent containing principally isobutene and n-butenes. Preferably, said C$_5$ cut has previously undergone selective hydrogenation of the polyunsaturated compounds and hydroisomerisation of the monoolefins, advantageously obtained simultaneously with hydrogenation. Metathesis is carried out in the presence of a catalyst comprising (and preferably constituted by) delta alumina, rhenium and cesium. Preferably, the catalyst comprises at least one rhenium compound deposited on a support composed principally by alumina which has been treated at a temperature of more than 750° C., so as to transform a portion of the alumina to delta alumina, and modified by at least one cesium compound. Metathesis takes place at a temperature in the range 20° C. to 1 50° C., and at a pressure at least equal to the vapour tension of the reaction mixture at the reaction temperature, and is followed by separation of the isobutene produced.

The catalyst used in the process of the invention thus comprises (and is preferably constituted by) at least three components:

a porous alumina-based support; more generally, the support is principally composed by alumina, and advantageously it contains at least 75% by weight of alumina, preferably it is constituted by alumina, with at least a portion of the alumina being delta alumina (at least 0.5% by weight and preferably at least 1% by weight, or more preferably, 5% by weight and preferably 5–50% by weight)

0.01% to 20% by weight of rhenium;

and 0.01% to 5% by weight of cesium.

In this catalyst preparation process, a catalyst precursor based on gamma alumina and rhenium is formed and said precursor undergoes heat treatment at more than 750° C. in a non reducing gas atmosphere. In one implementation, the precursor also contains cesium. In a preferred implementation, the precursor containing rhenium but not cesium, which has been heat treated at more than 750° C., is impregnated with a cesium compound, dried than activated.

The porous starting support is based on gamma alumina, and advantageously has an appreciable surface area, for example at least 10 m$^2$/g, and preferably at least 50 m$^2$/g, and a sufficient pore volume, for example at least 0.1 ml/g, preferably 0.3–1 ml/g.

The rhenium compound can be introduced into the support, for example by vapour phase sublimation or by impregnation in solution. In general, the dry impregnation method is preferably used, where the rhenium compound is dissolved in water or in an organic solvent, for example a hydrocarbon, an alcohol or an ether. The quantity of rhenium on the support is adjusted by selecting the concentration of the impregnating solution. When the quantity of rhenium which is to impregnated is higher than that which a solution at its saturation limit will allow, the operation must be carried out several times with intermediate drying steps to eliminate the impregnation solvent, at a temperature of 90° C. to 250° C., for example, preferably 100° C. to 180° C. This enables 0.01% to 20%, preferably 0.1% to 15%, more advantageously 0.5% to 8% by weight of metallic rhenium, to be introduced. Preferred rhenium compounds are rhenium heptoxide, ammonium perrhenate and perrhenic acid.

After the rhenium impregnation step, a catalyst precursor is obtained, then drying is carried out at a temperature of 90° C. to 250° C., for example, preferably 100° C. to 180° C., followed by calcining at a temperature of more than 750° C. and advantageously at most 1000° C., preferably 900° C., in a non reducing gas atmosphere, for example oxygen, nitrogen or argon, oxygen diluted with nitrogen, preferably in air, under static or dynamic conditions, a slow gaseous stream being preferable, however. The amount of moisture in the gaseous stream is preferably kept below 200 ppm (parts per million). However, it is possible to heat in an atmosphere constituted by methane combustion gases or a natural gas in the presence of an excess of air. The duration of this activation treatment is, for example, from 10 minutes to 5 hours or more, after which the precursor obtained is cooled in an atmosphere which is preferably anhydrous. During this calcining treatment, a portion of the gamma alumina is transformed into delta alumina, for example at least 0.5% by weight, preferably 5% to 50% by weight of delta alumina with respect to the starting alumina.

The cesium compound can be introduced into the support using any of the usual methods used in heterogeneous catalysis, for example by solution impregnation. In general, it is preferable to use the dry impregnation method, described above. The cesium compound is dissolved in water. The volume of the solution is less than or at a maximum equal to the volume of the pores of the support. The quantity of cesium on the support is adjusted by selecting the concentration of the impregnation solution. When the quantity which is to be impregnated is higher than that which can be introduced by a solution at its saturation limit, the operation must be carried out several times, with intermediate drying steps to eliminate the impregnation solvent, at a temperature of 90° C. to 250° C., for example, preferably 100° C. to 180° C. This enables 0.01% to 5%, preferably 0.1% to 3%, and more advantageously 0.2% to 2% by weight of metallic cesium to be introduced. The cesium compound is advantageously a salt such as a halide or a sulphate, preferably a nitrate.

The catalytic composition obtained following the preceding steps is activated by heating between 400° C. and 1000° C., preferably between 500° C. and 900° C., and more preferably between 400° C. and 600° C. If the temperature is increased beyond 750° C., delta alumina formation is observed, but also rhenium is lost due, it appears, to the presence of the cesium. This heating is carried out in a non reducing gas atmosphere, for example: oxygen, nitrogen or argon, oxygen diluted with nitrogen, preferably in air, under static or dynamic conditions, a slow stream of gas being preferable, however. The amount of moisture of the gas stream is preferably kept below 200 ppm (parts per million). The duration of the activation treatment is, for example, 10 minutes to 5 hours or more, after which the active catalyst obtained is cooled in an atmosphere which is preferably anhydrous. Advantageously, a nitrogen purge is carried out, if necessary, before bringing it into contact with the hydrocarbon-containing feed.

In the process, the metathesis reaction is preferably carried out in the liquid phase, in the absence of oxygen, oxygen-containing compounds, nitrogen-containing compounds or sulphur-containing compounds and moisture, at a temperature in the range 20° C. to 150° C., preferably in the range 20° C. to 100° C., and at a pressure of at least the vapour tension of the reaction mixture at the reaction temperature.

The catalyst can be used in a fixed bed. In this case, as it has to be regenerated frequently, it is then necessary to provide at least two reactors in parallel, one being in operation while the other is being regenerated. It is also possible to use a moving catalytic bed system such as that described in French patent FR-A-2 608 595. The catalyst is extracted at regular time intervals from the bottom of the reactor and transferred to a continuous regeneration system, from which the regenerated catalyst is returned to the top of the reactor.

Because of the limits imposed by thermodynamics, the unconverted reactants are fractionated and can be recycled to the metathesis reactor.

The following example illustrates the invention without limiting its scope.

EXAMPLE 1

A metathesis catalyst was prepared by dry impregnation of a gamma alumina with a specific surface area of 180 m$^2$/g using an aqueous perrhenic acid solution (rhenium metal content: 54.08% by weight) so as to obtain a catalyst containing about 8% by weight of rhenium. The impregnated solid was dried for 12 hours statically at a temperature of 120° C., then placed in a furnace flushed with a gas constituted by combustion gases from a natural gas burner in the presence of excess air, and where the temperature was gradually increased to 800° C. After a constant stage at this temperature lasting 15 minutes. The catalyst was cooled to ambient temperature in a stream of dry nitrogen.

The catalyst was then modified by introducing cesium. To this end, it was dry impregnated with an aqueous cesium nitrate solution the concentration of which was such that about 0.5% of cesium was introduced into the catalyst. When the impregnation operation was completed, the solid was dried for 12 hours under static conditions at a temperature of 120° C., then placed in a furnace flushed with a stream of air, and the temperature was gradually increased to 550° C. After a constant temperature stage lasting 2 hours at this temperature, the catalyst was cooled to ambient temperature in a stream of dry nitrogen. The catalyst obtained contained 7.75% of rhenium and 0.55% of cesium (in % by weight expressed as the metal).

The metathesis reaction was carried out in a continuous pilot unit comprising a stainless steel tube reactor charged with 150 g of catalyst as prepared above. The reactant stream was constituted by ethylene and by a $C_5$ cut which had previously undergone selective hydrogenation and hydroisomerisation. Its composition was as follows:

| | |
|---|---|
| Saturated compounds | 57.5% by weight |
| Cyclopentene | 3.6 |
| Trans-2-pentene | 3.6 |
| 2-methyl-2-butene | 22.7 |
| 1-pentene | 0.8 |
| 2-methyl-1-butene | 3.0 |
| Cis-2-pentene | 2.8 |

The quantity of ethylene introduced was such that the mole ratio of ethylene to $C_5$ olefins was equal to 1:1. The total flow rate through the reactor was 150 g/h. The temperature was fixed at 35° C. and the pressure was adjusted to 35 bars. After 18 hours of operation, the conversion of 2-methyl-2-butene was 65%, the conversion of trans-2- pentene was 75% and the conversion of cis-2-pentene was 86%. The propylene + butenes yield was stable at 1.5–1.7 g/g of Re/h up to 40 hours of operation, then started to decrease rapidly thereafter. In an industrial operation, it would then be necessary to regenerate the catalyst, and the operating cycle duration would be 40 hours.

What is claimed is:

1. In a process comprising catalytically metathesizing a $C_5$ olefinic cut with ethylene or propylene to produce isobutene, the improvement wherein a catalyst for metathesizing a $C_5$ olefinic cut comprises delta alumina, rhenium and cesium.

2. A process according to claim 1, characterized in that said $C_5$ olefinic cut has first undergone selective hydrogenation of polyunsaturated compounds and hydroisomerisation of monoolefins.

3. A process according to claim 1, in which the catalyst comprises at least one rhenium compound deposited on a support principally composed of alumina which has been heat-treated at a temperature of more than 750° C. and then modified by at least one cesium compound.

4. A process according to clam 3, characterized in that the heat treatment after impregnation of the rhenium is carried out at a temperature of more than 750° C. to at most 1000° C., in a non reducing gas atmosphere, so as to transform at least 0.5% of the gamma alumina into delta alumina.

5. A process according to claim 1, characterized in that metathesis takes place at a temperature in the range 20° C. to 150° C., and at a pressure at least equal to the vapour tension of the reaction mixture at the reaction temperature.

6. A process according to claim 1, characterized in that the cesium content of the catalyst is 0.01% to 5% by weight, expressed as the cesium metal.

7. A process according to claim 1, characterized in that the rhenium content of the catalyst is 0.01% to 20% by weight, expressed as the rhenium metal.

8. A process according to claim 3, characterized in that the support contain at least 75% by weight of alumina, with a surface area of at least 10 m²/g and a pore volume of at least 0.1 ml/g.

9. A process according to claim 3, further comprising impregnating the support with a rhenium compound selected from the group consisting of rhenium heptoxide, ammonium perrhenate and perrhenic acid.

10. A process according to claim 3 wherein the cesium compound is a halide, a sulphate or a nitrate.

11. A process according to claim 1, wherein the catalyst is constituted by alumina, rhenium and cesium and comprising at least 0.5% by weight of delta alumina.

12. A process according to claim 1, wherein the alumina contains 5–50% by weight of delta alumina.

13. A process according to claim 12, characterized in that the cesium content of the catalyst is 0.01% to 5% by weight, expressed as the cesium metal.

14. A process according to claim 12, characterized in that rhenium content of the catalyst is 0.01% to 20% by weight, expressed as the rhenium metal.

15. A process according to claim 13, characterized in that rhenium content of the catalyst is 0.01% to 20% by weight, expressed as the rhenium metal.

16. In a process comprising catalytically metathesizing a $C_5$ olefinic cut with ethylene or propylene to produce isobutene, the improvement wherein a catalyst for metathesizing a $C_5$ olefinic cut consists essentially of delta alumina, rhenium and cesium.

17. A process according to claim 1, wherein the cesium content of the catalyst is 0.01% to 3% by weight, expressed as the cesium metal.

18. A process according to claim 1, wherein the cesium content of the catalyst is 0.02% to 2% by weight, expressed as the cesium metal.

19. A process according to claim 3, wherein the support contains a pore volume of 0.3–1 ml/g.

20. A process according to claim 16, wherein the cesium content of the catalyst is 0.02% to 2% by weight, expressed as the cesium metal.

* * * * *